United States Patent

Weikard et al.

[11] Patent Number: 6,150,458
[45] Date of Patent: Nov. 21, 2000

[54] PROCESS FOR PREPARING ESTERS OF (METH) ACRYLIC ACID

[75] Inventors: Jan Weikard, Köln; Wolfgang Fischer, Meerbusch, both of Germany

[73] Assignee: Bayer Aktiengesellschaft, Leverkusen, Germany

[21] Appl. No.: 09/358,303

[22] Filed: Jul. 21, 1999

[30] Foreign Application Priority Data

Jul. 30, 1998 [DE] Germany ............... 198 34 360

[51] Int. Cl.$^7$ ............... C08G 63/91; C08G 65/32
[52] U.S. Cl. ............... 525/31; 525/20; 525/23; 525/42; 525/404; 525/407; 525/438; 525/445; 525/921; 528/303; 528/365; 528/366
[58] Field of Search ............... 525/31, 42, 20, 525/23, 404, 407, 438, 445, 921; 528/303, 366, 365

[56] References Cited

U.S. PATENT DOCUMENTS 5,096,938  3/1992  Beck et al. ............... 522/100
5,602,191  2/1997  Reich et al. ............... 522/174

FOREIGN PATENT DOCUMENTS 0 054 105  12/1984  European Pat. Off. .
0 126 341   2/1989  European Pat. Off. .

*Primary Examiner*—Patricia A. Short
*Attorney, Agent, or Firm*—Joseph C. Gil; Thomas W. Roy

[57] ABSTRACT

The present invention relates to a process for preparing (meth)acrylic acid esters by 1) reacting hydroxyl group-containing polyethers, polyesters or polyester ethers with (meth)acrylic acid in the presence of an acid esterification catalyst and a solvent to form (meth)acrylic acid esters, and 2) reacting the acid esterification catalyst acid and unreacted (meth)acrylic acid with a compound containing two or more epoxide groups in the presence of the solvent used in step 1).

16 Claims, No Drawings

PROCESS FOR PREPARING ESTERS OF (METH) ACRYLIC ACID

DETAILED DESCRIPTION OF THE INVENTION

1. Field of the Invention

The invention relates to a process for preparing (meth) acrylates, i.e., esters of propenoic acid and 2-methylpropenoic acid.

2. Description of the Prior Art

Esters of (meth)acrylic acid, e.g. (2-methyl)propenoic acid, are used in coating technology for preparing binders which can be cured by high-energy radiation. They should have as low a concentration as possible of free (2-methyl) propenoic acid.

It is known that polyesters which contain hydroxyl groups can be azeotropically esterified with (meth)acrylic acid using acid catalysis. In this case, after removing the solvent, unreacted (2-methyl)propenoic acid is chemically bonded using epoxides (oxirane compounds) as described, e.g., in EP-A 54,105, 126,341. These processes have the following disadvantages. In the process described in EP-A 54,105, (meth)acrylic acid is only used in less than stoichiometric amounts (max. 90 mol. % with respect to the OH groups of the polyester), so that the products produced have undesirably high viscosities due to the residual concentration of hydroxyl groups.

The process described in EP-A 126,341 also requires neutralization of the esterification catalyst with alkali metal hydroxides or tertiary amines prior to separating non-esterified (meth)acrylic acid with epoxides. Because the residues of the low molecular weight compounds arising from the esterification catalyst and neutralising agent cannot be copolymerized with (meth)acrylate, they are detrimental to the hardness and resistance of the resulting coatings. Furthermore, tertiary amines have an adverse affect during the UV curing of binder compositions (P. K. T Oldring, Chemistry & Technology of TV & EB Formulations for Coatings, Ink & Paints, 1991, pp. 192–196). Thus, their presence in the coating raw materials is undesirable.

It is also disadvantageous that the solvent has to be removed by distillation before the non-esterified (meth) acrylic acid can be reacted with epoxide-containing compounds at elevated temperatures of up to 130° C. The high temperatures are also undesirable since spontaneous and unwanted polymerization of the (meth)acrylic acid can take place and this is difficult to control due to the lack of evaporative cooling which is normally provided by the solvent.

Therefore, it is an object of the present invention to provide a process for preparing (meth)acrylates (esters of (2-methyl)propenoic acid) which does not have the disadvantages of the prior art processes.

This object may be achieved with the process of the present invention in which after the esterification of the hydroxyl group-containing polyesters or polyethers with (meth)acrylic acid, both the acid catalyst and unreacted (meth)acrylic acid are reacted in the esterification solvent with dimeric or oligomeric oxirane compounds (epoxides) until an acid number of less than or equal to 5 mg KOH/g is obtained. The solvent is then removed from the reaction mixture by distilling under reduced pressure (down to $10^{-5}$ bar). Thermal stress in the concentrated (meth)acrylate remains low so that spontaneous, undesired polymerization of the (meth)acrylates prepared is substantially avoided.

SUMMARY OF THE INVENTION

The present invention relates to a process for preparing (meth)acrylic acid esters by
1) reacting hydroxyl group-containing polyethers, polyesters or polyester ethers with (meth)acrylic acid in the presence of an a
2) reacting the acid esterification catalyst acid and unreacted (meth)acrylic acid with a compound containing two or more epoxide groups in the presence of the solvent used in step 1).

DETAILED DESCRIPTION OF THE INVENTION

Acrylic acid (propenoic acid) or methacrylic acid (2-methyl-propenoic acid) or mixtures thereof may be used for the process according to the invention.

The polyesters used for the process according to the invention are those in which the alcohol component is selected from monohydric or polyhydric, saturated, aliphatic or cycloaliphatic $C_1$–$C_{20}$ alcohols which may also contain ether groups. These alcohols have number average molecular weights of 32 to about 800. Examples include methanol, ethanol, the isomeric propanols, butanols and hexanols, cetyl alcohol, stearyl alcohol, ethylene glycol, propylene glycol, butanediol-1,4, pentanediol-1,5, neopentyl glycol, hexanediol-1,6, glycerol, trimethylolethane, trimethylolpropane, pentaerythritol, 2-ethylhexanol, cyclohexanol, dimethylolcyclohexane and alkoxylation products of these alcohols with 1 to 5 moles of ethylene oxide or propylene oxide per hydroxyl group.

The acid component in these polyesters is selected from saturated $C_1$–$C_{20}$ aliphatic or $C_6$–$C_{24}$ aromatic carboxylic acids. Examples include monocarboxylic acids such as benzoic acid and dicarboxylic acids such as succinic acid, glutaric acid, adipic acid, phthalic acid, isophthalic acid, terephthalic acid and substituted phthalic acids. The corresponding acid anhydrides may also be used.

Acidic esterification catalysts for use in the process according to the invention include inorganic or organic acids, which are used in an amount of 0.1 to 3 wt. %, based on the weight of (meth)acrylic acid to be esterified. Examples of suitable esterification catalysts include sulfuric acid, phosphoric acid, pyrophosphoric acid, p-toluenesulfonic acid, styrene-divinylbenzenesulfonic acid, chlorosulfonic acid and chloroformic acid. Sulfuric acid and p-toluenesulfonic acid are preferred.

The process according to the invention is carried out in a solvent that is not miscible with water and can be distilled with water in a steam distillation process. Suitable solvents include hydrocarbons optionally substituted with halogen or nitrogen and other solvents which do not react with the reactants and are not modified in the presence of the acid catalysts. Preferably, unsubstituted hydrocarbons are used.

Examples of suitable solvents include aliphatic hydrocarbons such as hexane, heptane, octane and petroleum fractions having various boiling ranges; cycloaliphatic hydrocarbons such as cyclopentane, cyclohexane and methylcyclohexane; and aromatic hydrocarbons such as benzene, toluene and the isomeric xylenes. Preferred solvents are those which boil within the range of 70 to 120° C. Especially preferred are cyclohexane, toluene and petroleum fractions which boil within the range of 70 to 120° C. The solvent which is not miscible with water may be a mixture of the above mentioned solvents. See Le A 33 135 p. 4 lines 3 to 4. They are used in an amount of 10 to 100 wt. %, preferably 15 to 50 wt. % and more preferably 20 to 40 wt. %, based on the weight of reaction components to be esterified.

In one embodiment of the present invention, hydroxyl group-containing polyesters are prepared by the solvent-free melt condensation of the previously described alcohol and carboxylic acid components. This reaction precedes the process according to the invention in which the polyester is esterified with (meth)acrylic acid in one of the preceding solvents. It another embodiment of the present invention the polyesters are prepared in the same solvent used for the reaction with (meth)acrylic acid. The reaction water is then removed from the reaction mixture by boiling solvent.

The process according to the invention may be performed in the presence of one or more polymerization inhibitors in an amount of 0.01 to 1 wt. %, preferably 0.1 to 0.5 wt. %, based on the weight of the reactants. Suitable inhibitors are described, for example, in Houben-Weyl, Methoden der organischen Chemie, 4th edition, vol. XIV/1, Georg Thieme Verlag, Stuttgart 1961, page 433 et seq. Examples include sodium dithionite, sodium hydrogen sulfate, sulfur, hydrazine, phlenyhydrazine, hydrazobenzene, N-phenyl-β-naphthylamine, N-phenyl-ethanolamine, dinitrobenzene, picric acid, p-nitroso-dimethylaniline, diphenylnitrosamine, phenols (such as p-tert.-butyl-pyrocatechol, 2,5-di-tert.-amylhydroquinone, p-alkoxyphenols and di-tert.-butylhydroquinone), tetramethyl-thiuram disulfide, 2-mercaptobenzthiazol and the sodium salt of dimethyl-dithiocarbamic acid.

In a preferred embodiment of the process according to the invention, an oxygen-containing gas, preferably air, is passed through the solvent-containing reaction mixture.

According to the process of to the invention, (2-methyl) propenoic acid is first esterified at a temperature of 60 to 140° C., preferably 70 to 120° C. and more preferably at the boiling point of the solvent used. The solvent is continuously distilled from the reaction mixture, separated from entrained water in a water separator outside the reaction vessel and then returned to the reaction mixture. The reaction is complete when the amount of water corresponding to the desired degree of conversion for the reaction has been separated or the acid number of the reaction mixture has fallen to a value corresponding to the desired degree of conversion. This corresponds to a degree of conversion of 60 to 100%, preferably 70 to 89% and more preferably 75 to 84%, based on the OH groups in the hydroxyl group-containing compound.

After completion of esterification and before neutralizing the catalyst or distilling off the solvent, the reaction of any unreacted (meth)acrylic acid with the compounds containing two or m ore epoxide groups, e.g., dimeric or oligomeric epoxide (oxirane) compounds, takes place. This is performed at temperatures of 50 to 129° C., preferably 70 to 99° C. and more preferably 80 to 89° C.

Examples of suitable (oligo)epoxides include dimeric or oligomeric epoxides (oxirane compounds) such as glycidyl ethers or esters of aliphatic or aromatic polyols or polyacids such as hexanediol bis-glycidyl ether, bis-phenol A bis-glycidyl ether, the bis-glycidyl ester of hexahydrophthalic acid, glycerol triglycidyl ether and pentaerythritol triglycidyl ether.

In accordance with the present invention the epoxides are added in a molar ratio of oxirane groups to acid groups (from both the acid catalyst and non-esterified (2-methyl) propenoic acid, which can be determined by determining the acid number of the reaction mixture) of 2:1 to 1:1, preferably 1.4:1 to 1.1:1 and more preferably 1.2:1. The reaction is continued until the acid number has fallen to less than 5 (mg KOH/g of substance).

The reaction of epoxides with acid catalyst and non-esterified (meth)acrylic acid may take place in the presence of other catalysts. Suitable catalysts include quaternary ammonium halides such as tetrabutylamnonium bromide or iodide; triphenylphosphine; phosphonium salts such as eth-yltriphenylphosphonium iodide; and alkali metal halides such as potassium iodide.

The (meth)acrylates prepared according to the invention are used as binders in radiation-curable or conventionally cured sealing and coating compositions.

The invention is further illustrated but is not intended to be limited by the following examples in which all parts and percentages are by weight unless otherwise specified.

EXAMPLES

Example 1

An ether group-containing acrylate (propenate)

775 g of a polyether triol, which was prepared from one mole of trimethylolpropane and 4 moles of ethylene oxide, 468 g of propenoic acid, 1.5 wt. % (based on the weight of polyol and propenoic acid) of p-toluenesulfonic acid, 3000 ppm of p-methoxyphenol and 200 ppm of 2,5-di-tert.-butyl-hydroquinone were mixed with 400 g of isooctane with stirring. While air was passed through the mixture at a rate of a single tank volume per hour and nitrogen was passed over the mixture at a rate of two tank volumes per hour, the mixture was heated up to reflux temperature (about 100° C.) with constant stirring. The reaction water was separated and reflux was maintained until an acid number of about 5 mg KOH/g was obtained.

The apparatus was cooled to 85° C. and 15 g of bisphenol A-diglycidyl ether was added at 85° C. while air was passed through and nitrogen was passed over the mixture at the preceding rate. The mixture was held at a temperature of 85° C. for 2 hours. Then the solvent was distilled off under reduced pressure. The resulting acrylate (propenate) was clear and had an acid number of <1 mg KOH/g and a viscosity of 164 mPa.s at 23° C.

Example 2

An ester group-containing acrylate (propenate)

A polyester was prepared by melt condensation by melting 321 g of adipic acid and 1616 g of a triol, which was prepared from one mole of trimethylolpropane and 4 moles of ethylene oxide, at 145° C. while nitrogen was passed over the mixture at a rate of a single tank volume per hour and stirred at this temperature for 4 hours while reaction water was distilled off. The temperature was then increased to 190° C. and held at this temperature until an acid number of less than 5 mg KOH/g was obtained. 760 g of the resulting polyester, 363 g of acrylic acid (propenoic acid), 1.0 wt. % based on the weight of polyol and propenoic acid) of p-toluenesulfonic acid, 3000 ppm of p-methoxyphenol and 200 ppm of 2,5-di-tert.-butyl-hydroquinone were mixed with 450 g of isooctane with stirring. While air was passed through the mixture at a rate of a single tank volume per hour and nitrogen was passed over the mixture at a rate of two tank volumes per hour, the mixture was heated to reflux temperature (about 100° C.) with constant stirring. The reaction water was separated and the residue was held at this temperature until an acid number of about 40 mg KOH/g was obtained.

At 90° C. 193 g of bisphenol A-diglycidyl ether and, as catalyst, 0.5 wt. %, based on solids, of triethylbenzylammonium chloride were added while air was passed through and nitrogen was passed over the mixture at the preceding rate. The mixture was held at 90° C. until an acid number of less than 5 mg KOH/g was obtained. Then the solvent was distilled off under reduced pressure. The resulting acrylate (propenate) was clear and had a viscosity of 1700 mPa.s at 23° C.

Comparison Example 760 g of the polyester described in example 2, 363 g of acrylic acid (propenoic acid), 1.0 wt. % (based on the weight of polyol and propenoic acid) of p-toluenesulfonic acid, 3000 ppm of p-methoxyphenol and 200 ppm of 2,5-di-tert.-butyl-hydroquinone were mixed with 450 g of cyclohexane with stirring. While air was passed through the mixture at a rate of a single tank volume per hour and nitrogen was passed over the mixture at a rate of two tank volumes per hour, the mixture was heated to reflux temperature (about 85° C.) with constant stirring. The reaction water was separated and reflux was maintained until an acid number of about 40 mg KOH/g was obtained. The catalyst was neutralized by adding an equivalent amount of N,N-dimethylethanolamine. Then the solvent was distilled off under reduced pressure.

193 g of bisphenol-A-diglycidyl ether and, as catalyst, 0.5 wt. %, based on solids, of triethylbenzylammonium chloride were added at 90° C. and the mixture was held at 90° C. while air was passed through and nitrogen was passed over the mixture at the preceding rate until an acid number of less than 5 mg KOH/g was obtained. The acrylate (propenate) produced was clear and had a viscosity of 1400 mPa.s at 23° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a (meth)acrylic acid ester which comprises
   1) reacting a hydroxyl group-containing polyether, polyester or polyester ether with (meth)acrylic acid in the presence of an acid esterification catalyst and a solvent to form a (meth)acrylic acid ester, and
   2) reacting the acid esterification catalyst acid and unreacted (meth)acrylic acid with a compound containing two or more epoxide groups in the presence of the solvent used in step 1).

2. The process of claim 1 which comprises conducting step 2) at a temperature of 70 to 99° C.

3. The process of claim 1 which comprises carrying out step 1) until 70 to 89% of the hydroxyl groups have reacted.

4. The process of claim 2 which comprises carrying out step 1) until 70 to 89% of the hydroxyl groups have reacted.

5. The process of claim 1 which comprises reacting a hydroxyl group-containing polyester or polyester ether with (meth)acrylic acid.

6. The process of claim 2 which comprises reacting a hydroxyl group-containing polyester or polyester ether with (meth)acrylic acid.

7. The process of claim 3 which comprises reacting a hydroxyl group-containing polyester or polyester ether with (meth)acrylic acid.

8. The process of claim 4 which comprises reacting a hydroxyl group-containing polyester or polyester ether with (meth)acrylic acid.

9. The process of claim 1 wherein said compound containing two or more epoxide groups comprises bisphenol A-diglycidyl ether.

10. The process of claim 2 wherein said compound containing two or more epoxide groups comprises bisphenol A-diglycidyl ether.

11. The process of claim 3 wherein said compound containing two or more epoxide groups comprises bisphenol A-diglycidyl ether.

12. The process of claim 4 wherein said compound containing two or more epoxide groups comprises bisphenol A-diglycidyl ether.

13. The process of claim 5 wherein said compound containing two or more epoxide groups comprises bisphenol A-diglycidyl ether.

14. The process of claim 6 wherein said compound containing two or more epoxide groups comprises bisphenol A-diglycidyl ether.

15. The process of claim 7 wherein said compound containing two or more epoxide groups comprises bisphenol A-diglycidyl ether.

16. The process of claim 8 wherein said compound containing two or more epoxide groups comprises bisphenol A-diglycidyl ether.

* * * * *